United States Patent
Schwarz et al.

(10) Patent No.: US 11,775,126 B2
(45) Date of Patent: Oct. 3, 2023

(54) MEDICAL PUMP WITH A DISPLAY

(71) Applicant: B. Braun Melsungen AG, Melsungen (DE)

(72) Inventors: Jan Schwarz, Melsungen (DE); Christoph Erlen, Kassel (DE); Stephan Hoevel, Kassel (DE); Norbert Koop, Rellingen (DE); Jan Sokoll, Nortorf (DE); Stefan Espenhahn, Hamburg (DE); Joachim Schuetz, Fulda (DE); Yvonne Fischbach, Grossenlueder (DE); Gerhard Schoeffel, Blaustein (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 17/852,520

(22) Filed: Jun. 29, 2022

(65) Prior Publication Data
US 2023/0004247 A1   Jan. 5, 2023

(30) Foreign Application Priority Data
Jul. 1, 2021 (DE) ............ 20 2021 103 528.5

(51) Int. Cl.
*G06F 3/045* (2006.01)
*A61M 5/142* (2006.01)

(52) U.S. Cl.
CPC ......... *G06F 3/045* (2013.01); *A61M 5/14228* (2013.01); *A61M 2205/3306* (2013.01); *A61M 2205/505* (2013.01); *A61M 2205/587* (2013.01)

(58) Field of Classification Search
CPC ...... G06F 1/1656; G06F 3/045; G06F 1/1637; G06F 1/1643; A61M 5/14228;
(Continued)

(56) References Cited

U.S. PATENT DOCUMENTS 7,833,213 B2 * 11/2010 Katz ................. A61M 16/0003
  604/67
8,700,421 B2 *  4/2014 Feng ...................... G16H 20/17
  705/2
(Continued)

FOREIGN PATENT DOCUMENTS

AU    2019271195 A1 * 11/2020 ............ A61M 39/28
CA        3155536 A1 *  6/2014 .......... A61M 5/1408
(Continued)

OTHER PUBLICATIONS

Search Report received in German Application No. 20 2021 103 528.5 dated Jun. 21, 2022, with translation, 6 pages.

*Primary Examiner* — Vinh T Lam
(74) *Attorney, Agent, or Firm* — Christopher A. Rothe; Culhane Meadows PLLC (57) ABSTRACT

A medical pump for conveying a medical liquid has a pump housing and a front lid hingedly arranged at the pump housing. The medical pump also has a lid housing and an operating element integrated in the lid housing. The operating element features a resistive touch element and a separate display element arranged at a parallel distance to the touch element. The touch element and the display element jointly form a touch screen, and are fastened at respectively opposing sides of the lid housing.

11 Claims, 5 Drawing Sheets

(58) Field of Classification Search
CPC ...... A61M 2205/505; A61M 2205/587; A61M 5/142; A61M 2205/3306; F04B 53/16; F04B 43/08
See application file for complete search history.

(56) References Cited

U.S. PATENT DOCUMENTS

| | | | | |
|---|---|---|---|---|
| 8,777,923 | B2* | 7/2014 | Katz | A61B 8/42 604/67 |
| 9,192,711 | B2* | 11/2015 | Barnes | A61M 5/16854 |
| 9,623,172 | B2* | 4/2017 | Barnes | A61M 5/1413 |
| 10,648,564 | B2* | 5/2020 | Slaby | A61M 5/14228 |
| 2009/0153058 | A1* | 6/2009 | Feng | G16H 20/17 315/76 |
| 2009/0157432 | A1* | 6/2009 | Palmroos | A61M 5/142 700/83 |
| 2014/0318542 | A1* | 10/2014 | Katz | A61B 5/4839 128/204.23 |
| 2015/0073338 | A1* | 3/2015 | Waldhoff | A61J 15/0026 604/67 |
| 2016/0228633 | A1* | 8/2016 | Welsch | G06F 3/015 |
| 2017/0181694 | A1* | 6/2017 | Niklewski | A61B 5/4839 |
| 2017/0182277 | A1* | 6/2017 | Niklewski | A61M 5/1723 |
| 2017/0185732 | A1* | 6/2017 | Niklewski | G16H 40/63 |
| 2018/0187782 | A1* | 7/2018 | Slaby | F16J 15/104 |
| 2019/0184072 | A1* | 6/2019 | Madden | A61M 1/72 |
| 2020/0271226 | A1* | 8/2020 | Slaby | F16J 15/104 |
| 2021/0187197 | A1* | 6/2021 | Zade | A61M 5/1723 |

FOREIGN PATENT DOCUMENTS

| | | | |
|---|---|---|---|
| CN | 211485982 U | | 9/2020 |
| CN | 211485983 U | | 9/2020 |
| CN | 112562823 A | * | 3/2021 |
| CN | 112562823 A | | 3/2021 |
| DE | 102019121843 A1 | | 2/2021 |
| WO | WO-2014100658 A1 | * | 6/2014 ......... A61M 5/1408 |

* cited by examiner

MEDICAL PUMP WITH A DISPLAY

CROSS-REFERENCE TO RELATED APPLICATION

This application claims priority under 35 U.S.C. § 119 to German Application No. 20 2021 103 528.5, filed Jul. 1, 2021, the content of which is incorporated by reference herein in its entirety.

FIELD

The disclosure relates to a medical pump, preferably a peristaltic pump or a syringe pump, for conveying a medical liquid with a foldable front lid with a display.

BACKGROUND

Known pumps comprise touch displays and/or screens and keys on which information may be output and instructions to the pump may be input by users. So, for instance, it is possible to input the correct drug and a dosage. In the case of a syringe pump it is possible to input the syringe model and the dosage of the drug.

CN 2 11 485 982 U and CN 2 11 485 983 U disclose medical pumps with a touch display as an input and output unit. The displays in the utility models mentioned comprise capacitive touch displays. Capacitive displays, however, have various disadvantages. On the one hand, it is not possible to operate capacitive displays with gloves or the like. Therefore, the user must take off the gloves before being able to make an input at the display. Furthermore, capacitive displays are susceptible to liquids. If (liquid) drops are present on the display surface, this may reduce the input quality of the display. Furthermore, liquid may penetrate into the display and may damage the display unit and/or electronics/a conductor plate behind the display.

SUMMARY

The object of the disclosure thus consists in remedying the disadvantages of the state of the art and in providing a medical pump with a display which is adapted to be operated with gloves and also seals a housing from the ingress of liquid.

The disclosure relates to a medical pump, preferably a peristaltic pump or a syringe pump, for conveying a medical liquid with a pump housing and a front lid which is arranged hingedly at the pump housing and comprises a lid housing and an operating element integrated in the lid housing. The operating element comprises a resistive touch element and a separate display element arranged at a parallel distance to the touch element which jointly form a touch screen, wherein the resistive touch element and the display element are fastened to respective opposing sides of the lid housing.

The pump comprises, in other words, the front lid with the lid housing. The front lid is adapted to be folded downwards in order that a tube or a syringe may be inserted in the pump. An operating unit being an input and output unit and being integrated into the lid housing is positioned in the front lid. The operating unit has a touch screen comprising a resistive touch element and a display element (mounted there below). The display element is arranged in the interior of the lid housing and the resistive touch element is arranged at the outer side of the lid housing facing the user. The display element is arranged in an interior of the lid housing such that it is protected from external influences/environmental influences by the lid housing and the resistive touch element, wherein the touch element serves quasi as a seal. For this purpose, the touch element is preferably larger than the display element, i.e. the circumferences thereof project preferably (two-dimensionally) beyond the display element, wherein these projecting sections of the circumference are in sealing contact with the lid housing.

The display element is sensitive to external influences. Therefore, it is arranged in the interior of the lid housing, where it is protected by the touch element and by the lid housing from liquids and pollutions, such as, for instance, dust. The resistive touch element is arranged at the outside of the lid housing such that a user may perform inputs on the touch element. Due to this arrangement the display element is protected in the interior of the lid housing.

The touch element thus protects the display element. The touch element is operable by the user from the outside of the lid housing. Since the touch element is resistive, it may also be operated with gloves. Due to the resistive touch element is it at all possible to separate the display element and the touch element spatially/constructively and to mount them to/in the housing from different sides.

In accordance with a further preferred feature of the disclosure the resistive touch element extends substantially over a whole operator-facing front side of the lid housing. The resistive touch element comprises additional operating keys positioned below the film and operated through the film.

The resistive touch element extends preferably over the entire face of a front shell of the lid housing. The operating keys are preferably pressure-actuated. With the operating keys it is, for instance, possible to open the front lid, to switch the pump on and off, to interrupt a pump program, and to switch the input of the pump to a home screen, and the like. The operating keys are preferably arranged independently of the touch element. The operating keys are preferably wired with a conductor plate/printed circuit board of the display element which is independent of the touch element.

It is further preferred that press-on foamed pieces are mounted to the rear wall of the front lid.

In accordance with a further preferred feature of the disclosure the touch element is glued to the front shell of the lid housing from the user-facing front side of the front lid. The touch element is, as already explained before, larger than the display face of the display element. This means that the touch element overlaps the front shell of the housing. The display element positioned behind the touch element is, through a recess clearance in a front of the front shell, visible from outside through the touch element. The touch element is consequently also larger than the recess clearance. Thus, there results a circumference face on which the touch element may be glued. The central overlapping of the recess clearance with the touch screen results in a large glue face. Due to this overlapping the touch element and/or the all-around gluing with the lid housing also ensures that no liquid/pollution may enter the interior of the housing.

In accordance with a further preferred feature of the disclosure the display element is screwed to the lid housing from the rear side. The display element is preferably screwed in the interior of the lid housing. For this purpose, the lid housing is divided into a front shell and a rear wall. The display element is screwed with the rear side of the front shell. Thus, the display element is protected by the front shell and by the touch element.

In accordance with a further preferred feature of the disclosure the touch element seals the housing from liquids and/or pollution. The touch element covers the entire face of the front shell. Since the touch element is glued with the lid housing, it is also tight with respect to liquids and dust. Thus, the touch element protects the components in the interior of the lid housing, for instance, the display element, the conductor plate, and plug connections.

In accordance with a further preferred feature of the disclosure a surface of the touch element is larger than a display face of the display element. The touch element does not only comprise the area directly above the recess clearance in the front shell, which is the visible area of the display element, but also the keys arranged next to the display field.

In accordance with a further preferred feature of the disclosure the display element is visible through a recess clearance in the lid housing, and the display element is larger than the recess clearance. The display element has a larger face than is the size of the recess clearance in the front shell of the lid housing. Thus, it is possible to compensate for manufacturing tolerances.

In accordance with a further preferred feature of the disclosure the operating unit comprises a conductor plate which is connected with electronics of the pump by a ribbon cable. The conductor plate is mounted on the display element. The conductor plate comprises a number of plug connections. A plug is the ribbon cable which connects the conductor plate with a power supply of the pump. By means of the ribbon cable the conductor plate is connected to the electronics of the pump. Thus, the conductor plate is supplied with current. Furthermore, the conductor plate is connected by the ribbon cable with a control unit of the pump. Accordingly, information may be transmitted via the ribbon cable.

In accordance with a further preferred feature of the disclosure, one or a plurality of pieces of a press-on foam are mounted on the rear wall of the front lid. The press-on foam is compressed once the front lid of the pump is closed. Once the locking of the front lid is released, the press-on foam expands and the front lid opens.

DETAILED DESCRIPTION

First Embodiment

Figure 1:
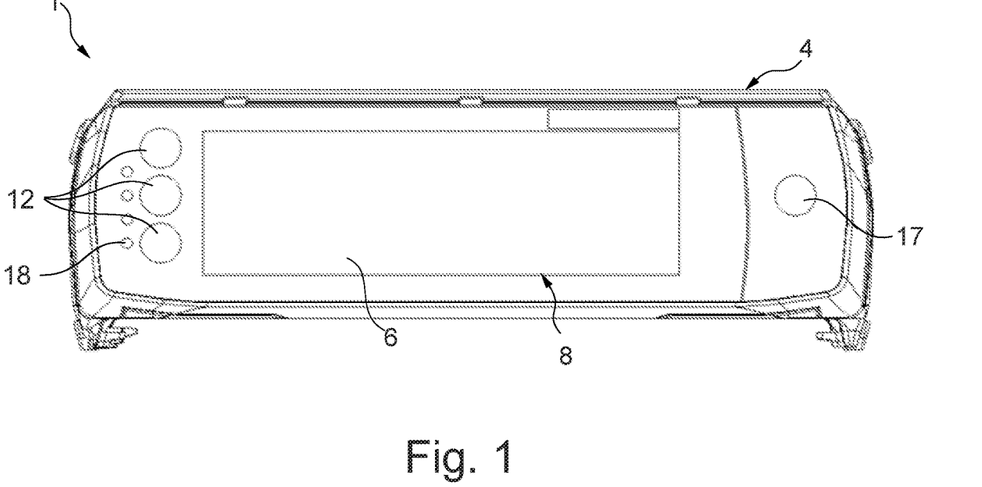
FIG. 1 shows a front view of a medical peristaltic pump with a touch screen in accordance with a first embodiment.

FIG. 1 shows a front view of a medical pump, preferably a peristaltic pump 1, with a front lid 4 adapted to be folded downwards from the pump 1. Due to the folding-down of the front lid 4 it is possible to insert a tube (not illustrated) in the pump 1. An operating unit 2 (illustrated in FIG. 7) is integrated in the front lid 4. The operating unit 2 comprises a touch element 6 and a display element 8. The front lid 4 comprises a lid housing 10 which is hingedly connected with the pump housing by means of hinges 12. The lid housing 10 comprises a rectangular recess clearance through which the display element 8 mounted in the lid housing 10 is visible. The rectangular recess clearance is thus a display field 14. At the user-facing side of the lid housing 10 a film 16 is applied into which the touch element 6 is integrated. The touch element 6 is substantially as large as the display field 14 in the lid housing 10. The touch element 6 is a resistive touch element via which a user may make input in the operating unit. The display element 8 outputs visual information to the user. The touch element 6 and the display element 8 jointly form a touch screen.

The film 16 comprises operating keys 12 which are positioned below the film 16. The film 16 is slightly elevated in these places and enables the pressing of the operating keys 12. One single key 17 is arranged at one side of the display field 14, by means of which the front lid 4 may be opened. At the other side of the display field 14 the plurality of operating keys 12 are arranged. The operating keys 12 are preferably arranged one above the other. Preferably, three operating keys 12 are arranged one above the other, one key with a home button, one key for switching the pump on and off, and one key with a stop button. Next to the operating keys 12, LED lights 18 are arranged which indicate different states of the pump 1. Preferably, three LED lights 18 are arranged in parallel to a short side of the display field 14. The LED lights 18, for instance, indicate whether the pump 1 is charged with a power supply, or output alerts to the user. A light sensor is arranged above the LED lights 18. In the places in which the LED lights 18 and the light sensor are positioned, the film 16 is transparent.

Figure 2:
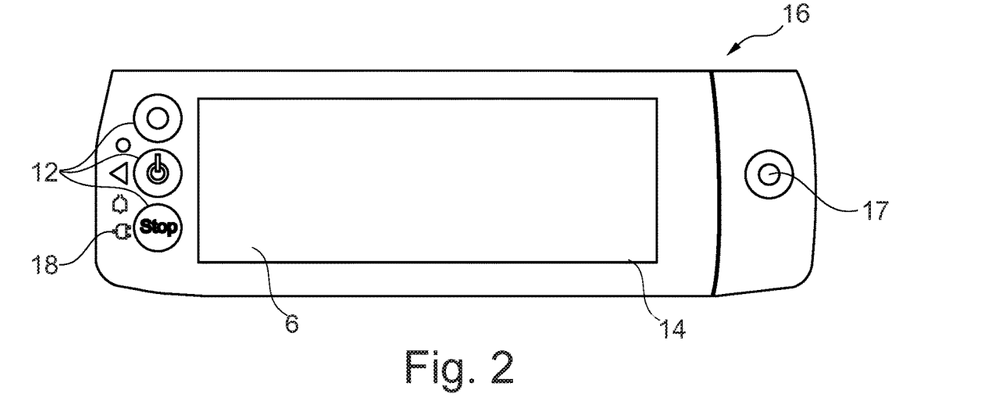
FIG. 2 shows a front view of a resistive touch element.

FIG. 2 shows the film 16 in accordance with the first embodiment. The film 16 is a thin film with an oval basic shape. The touch element 6 corresponds substantially to the shape of a user-facing front side of the lid housing 10. The touch element 6 is integrated in the film 16. In the middle, the touch element 6 comprises the rectangular transparent display field 14. The display element 8 is visible through the field. The touch element 6 is substantially positioned above the display field. The display element 8 is visible by a user through the touch element 6. The touch element 6 is approximately as large as the display field 14. The combination of the display element 8 and the touch element 6 which is integrated in the foil 16 and is substantially positioned above the display field 14 results in a touch screen. The operating keys 12 are arranged next to the transparent display field 14.

Figure 3A:
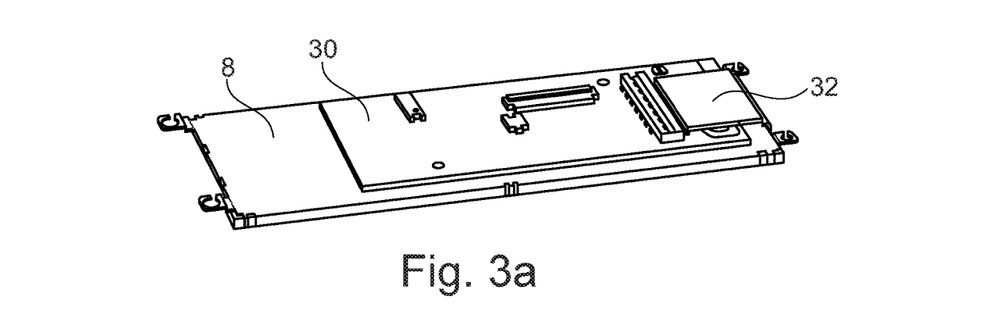
FIG. 3a shows an isometric view of a display element.

FIG. 3a shows an isometric view of the display element 8. The display element is a rectangular plate. At each corner of the rectangular plate a lug is arranged through which the display element 8 is screwed with the lid housing 10. At the rear side of the display element 8, i.e. at the side of the display element 8 which is not facing the user, a conductor plate 30 is positioned. The conductor plate 30 comprises a ribbon cable 32 which connects the display element 8 with the conductor plate 30.

Figure 3B:
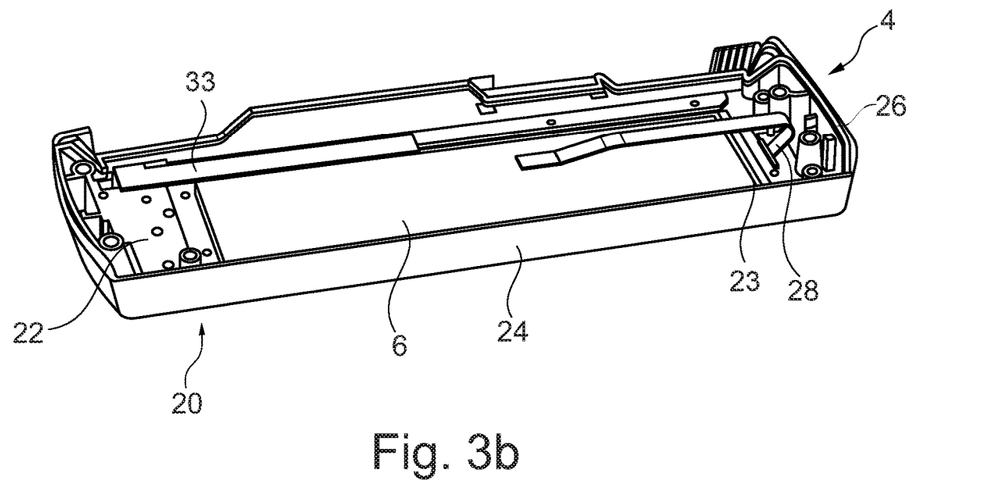
FIG. 3b shows a rear side of a front shell of a lid housing.

FIG. 3b shows a rear side of a front shell 20 of the lid housing 10. The front shell 20 comprises a flat front 22 and side walls 24 projecting from the front 22. The front has a rectangular recess clearance 23. At the top edge of the side walls 24 a seal 26 extends which seals the lid housing 10. The front shell 20 comprises the touch element 6 which is glued to the front shell 20 from the user-facing front side of the operating unit 2. The touch element 6 is positioned above the recess clearance 23 which results in the display field 14. Inside of the front shell 20 a cable 28 is arranged which connects the conductor plate 8 with the touch element 6. A further cable 33 connects the conductor plate 30 and the operating keys 12. The front shell 20 comprises docking sockets 35 (illustrated in FIG. 5) in which the display element 8 is screwed. The display element 8 is screwed with the front shell 20 from the rear side of the operating unit 2. Thus, the display element 8 is arranged in the interior of the lid housing 10 and is protected by the lid housing 10. The front shell 20 comprises columnar sockets for the screwing of a rear wall.

Figure 4:
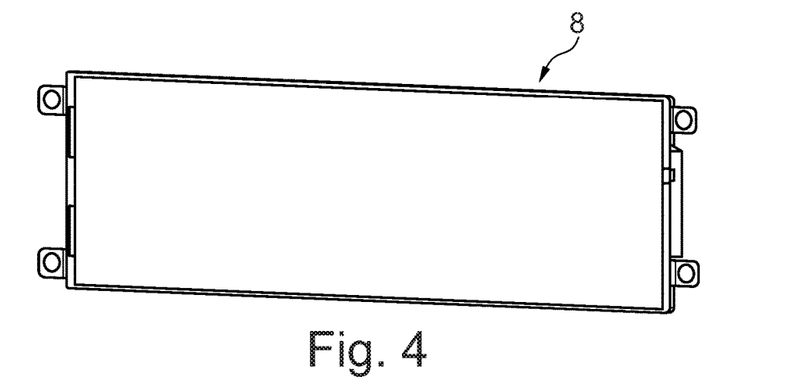
FIG. 4 shows the display element.

FIG. 4 shows a top view of the display element 8. The display element 8 is a flat rectangular plate. The display element 8 is a display such as, for instance, a LED or a LCD display. At each corner of the rectangle a lug is fastened through which a screw may be slid so as to fasten the display element 8 to the front shell 20. The display element 8 is an output element and outputs visual information to the user. The display element outputs, for instance, a dosage of the drug, the remaining time, the remaining drug volume, and the drug concentration.

Figure 5:
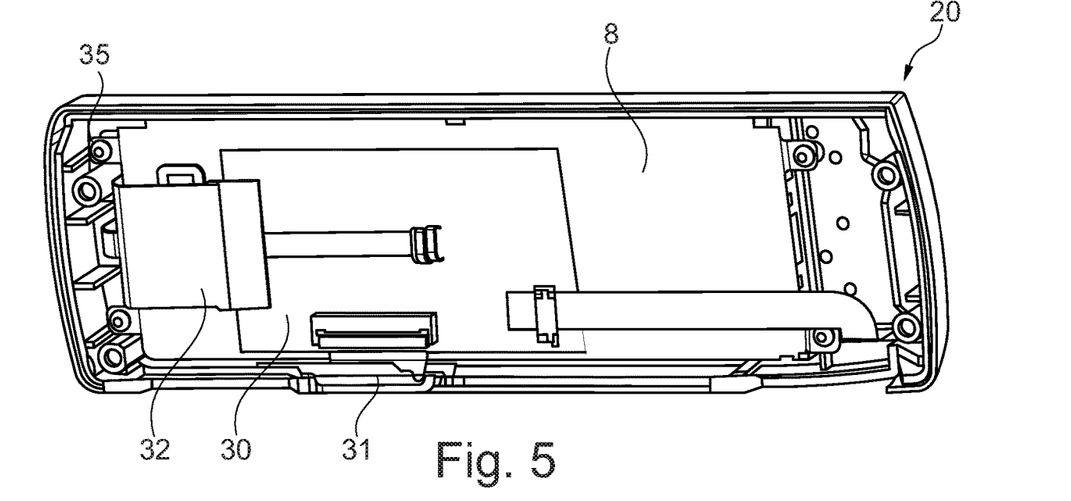
FIG. 5 shows a rear view of an operating unit with the display element.

FIG. 5 shows a rear side of the front shell 20 with the display element 8. In this view the display element 8 is screwed with the front shell 20. The conductor plate 30 is mounted on the display element 8. The conductor plate 30 is connected with the touch element 6 and the keys 12 by various connections/cables, for instance, the cables 32, 33. By means of a ribbon cable 31 the conductor plate 30 is connected to electronics of the pump 1 and to a control unit (not illustrated) of the pump 1.

Figure 6:
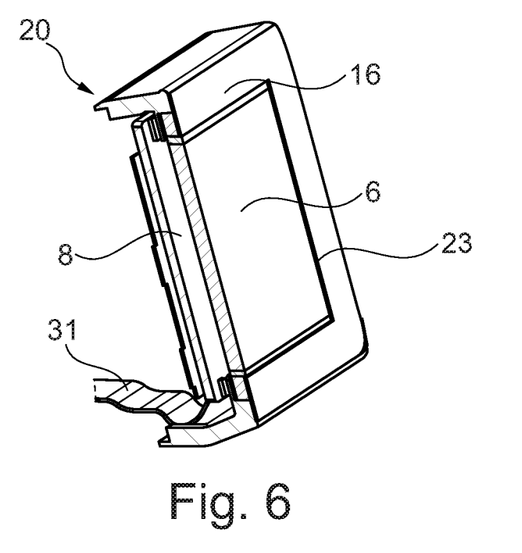
FIG. 6 shows a cross-section through the operating unit.

FIG. 6 shows a cross-section through the front shell 20 with the touch element 6 and the display element 8. The film 16 is fitted/glued to the front shell 20 from the front side of the front lid 4. The touch element is integrated in the film 16. The front 22 of the front shell 20 comprises the recess clearance 23 through which the display element 8 is visible. The touch element 6 is substantially positioned above the recess clearance 23. The display element 8 is connected from the rear side with the front shell 20. The display element 8 is larger than the recess clearance 23. Thus, it is possible to compensate for manufacturing tolerances. It is obvious that the film 16 extends over the recess clearance 23. The film 16 covers the front 22 of the front shell 20. Since the film 16 extends beyond the recess clearance 23, the film 16 seals the recess clearance 23 and hence the lid housing 10 from external influences.

Figure 7:
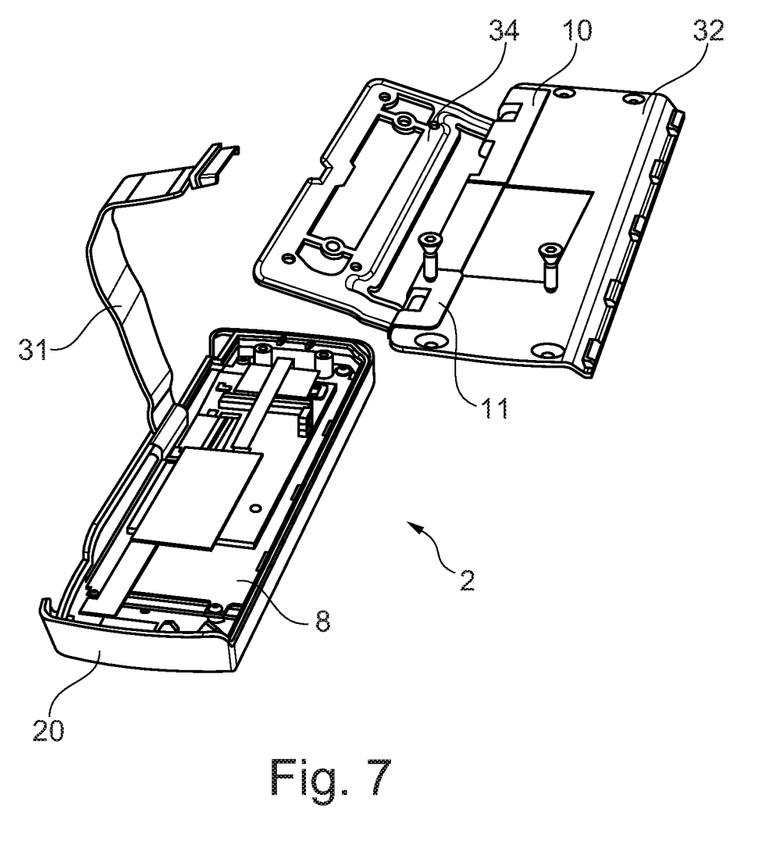
FIG. 7 shows the operating unit with a rear shell.

FIG. 7 shows a rear side of the operating unit 2 with the mounted display element 8. A rear wall 32 is fitted to the front shell 20 of the operating unit 2. The rear wall 32 is substantially a flat plate and is screwed with the front shell 20. The rear wall 32 protects the electronics in the lid housing 10. The seal 26 and the rear wall 32 result in a tight lid housing 10. The lid housing 10 with the seal 26 complies at least with the type of protection IP44. A metal hinge plate 34 is fastened to the rear wall 32. The hinge plate 34 is hingedly connected with the rear wall 32. This means that the hinge plate 34 may be tilted against the rear wall 32. The hinge plate 34 is connected with the pump housing. Thus, the front lid 4 is hingedly connected with the pump housing by means of the hinge plate 34.

Figure 8:
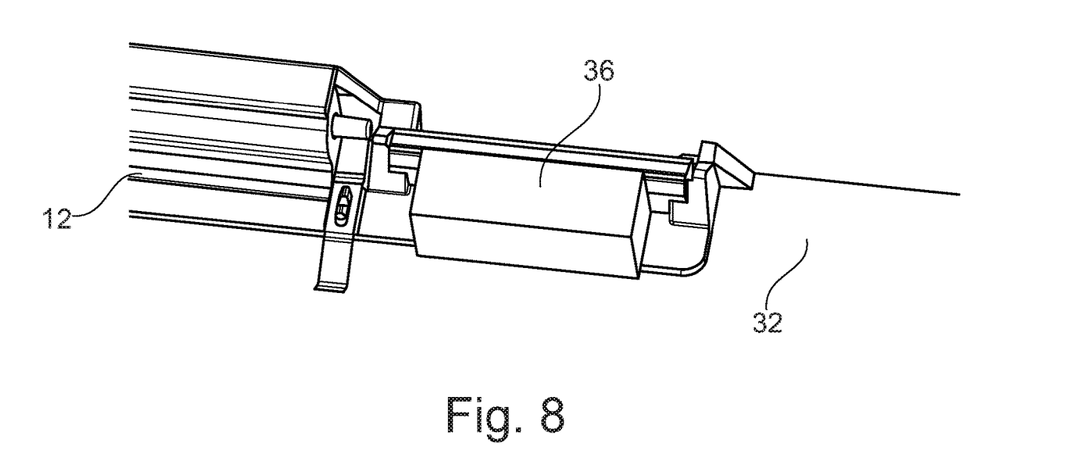
FIG. 8 shows a press-on foam at the rear shell.
Figure 9:
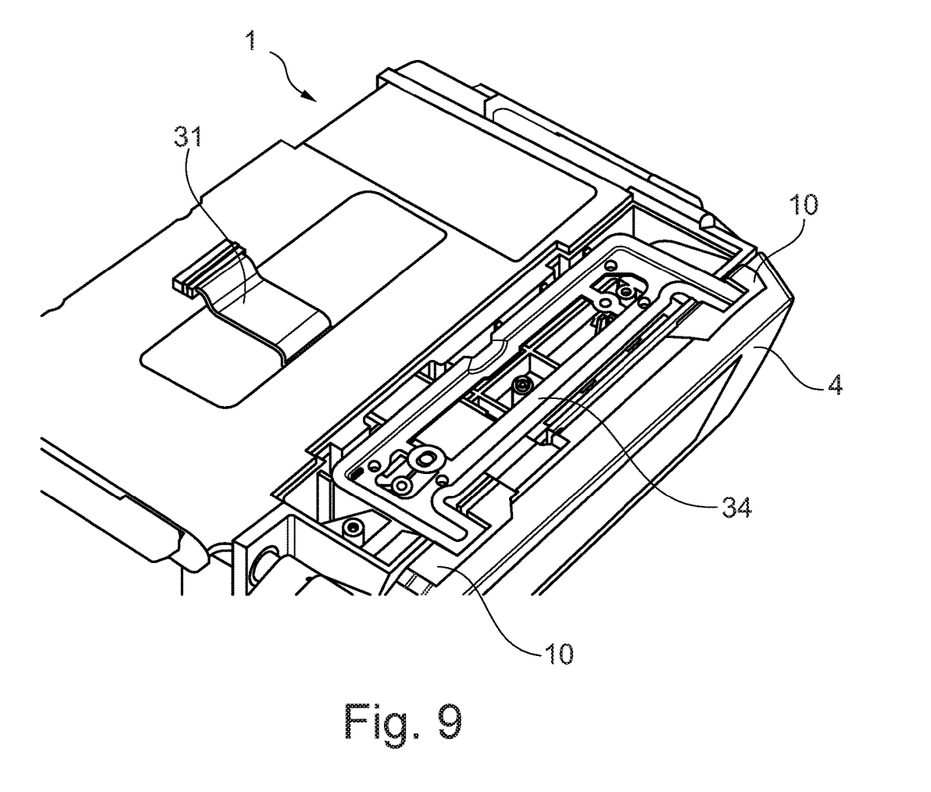
FIG. 9 shows a lower side of the pump with a hinge plate of the operating unit.

FIG. 8 shows the rear wall 32 with the hinge 11 and the press-on foam 36. The press-on foam 36 is arranged at the hinge 11 and is a rectangular piece of foam. The hinge 11 is arranged at the edge of the rear wall 32. The press-on foam 36 is arranged such that it rests on the front shell 20 in a manner centered with respect to the seal 26. The press-on foam pieces 36 terminate between the front lid 4 and the pump 1. The press-on foam pieces 36 are compressed when the front lid 4 is closed and expand when the front lid 4 is open. Thus, the front lid 4 is pressed open when a locking of the front lid 4 is opened. FIG. 9 shows a lower side of the pump 1. The hinge plate 34 is screwed with the pump housing. The hinge plate 34 is also connected with the front lid 4. Thus, the front lid 4 is hingedly connected with the pump 1. The ribbon cable 31 connects the conductor plate 30 with the electronics of the pump 1.

Second Embodiment

Figure 10:
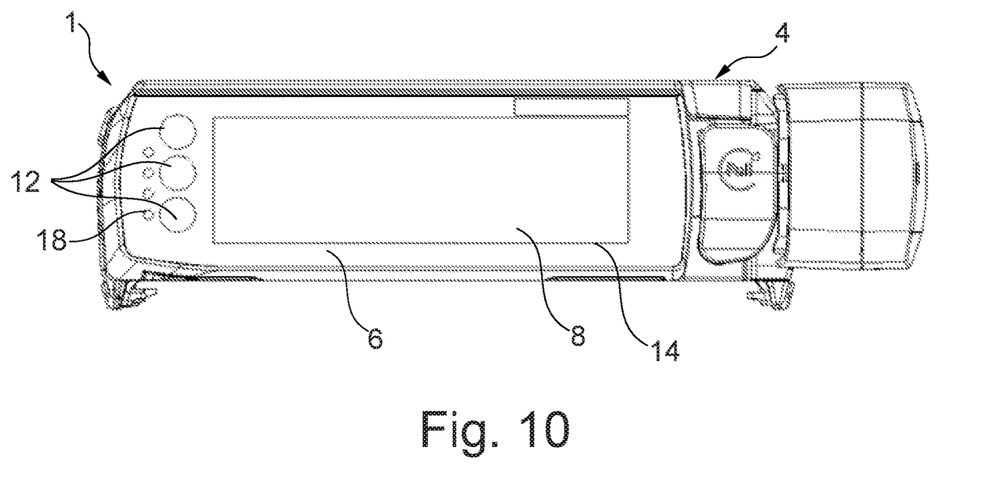
FIG. 10 shows a front view of a medical syringe pump with a touch screen in accordance with a second embodiment.

FIG. 10 illustrates a front view of a syringe pump. An operating unit 2 of the syringe pump 1 in accordance with a second embodiment comprises a rectangular display field 14 and a plurality of display keys 12. In comparison with the embodiment described before, the operating unit 2 in accordance with the second embodiment does not have any key for opening the lid. The operating keys 12 are identical with the superimposed operating keys 12 of the first embodiment. The function of the touch element 6 and of the display element 8 of the operating unit 2 is identical with the first embodiment. The design of the film 16 differs from the first embodiment since the door opening button 17 is missing. It is obvious that the design of the touch element 6 and the number of the keys 12 have not influence on the gist of the disclosure.

The invention claimed is:

1. A medical pump for conveying a medical liquid, the medical pump comprising:
   a pump housing;
   a front lid hingedly arranged at the pump housing;
   a lid housing; and
   an operating element integrated in the lid housing,
   the operating element comprising a resistive touch element and a display element arranged at a parallel distance to the resistive touch element,
   the resistive touch element and the display element jointly forming a touch screen, and
   the resistive touch element and the display element being fastened at respectively opposing sides of the lid housing.

2. The medical pump according to claim 1, wherein the resistive touch element is integrated in a film which extends substantially over a user-facing front side of the lid housing and comprises additional operating keys which are positioned below the film and are operated through the film.

3. The medical pump according to claim 2, wherein the front lid includes LED lights and a light sensor and in the places in which the LED lights and the light sensor are positioned, the film is transparent.

4. The medical pump according to claim 2, wherein the film is glued on the lid housing from the user-facing front side.

5. The medical pump according to claim 2, wherein the film simultaneously forms a seal protecting the display element from pollution and liquid from outside.

6. The medical pump according to claim 1, wherein the display element is visible through a recess clearance in the lid housing through the resistive touch element and the display element is larger than the recess clearance.

7. The medical pump according to claim 1, wherein the display element comprises a conductor plate which is connected to electronics of the pump by a ribbon cable.

8. The medical pump according to claim 1, wherein press-on foam pieces are mounted as sealing elements at a rear wall of the front lid.

9. The medical pump according to claim 1, wherein the lid housing is divided into a front shell and a rear wall and the display element is screwed to a rear side of the front shell.

10. The medical pump according to claim 9, wherein the resistive touch element covers an entire face of the front shell.

11. The medical pump according to claim 1, wherein the display element is screwed and/or glued to an inner side of the lid housing.

* * * * *